United States Patent
Kulstad et al.

(10) Patent No.: US 10,736,773 B2
(45) Date of Patent: Aug. 11, 2020

(54) DEVICES, SYSTEMS, AND METHODS FOR MANAGING PATIENT TEMPERATURE AND CORRECTING CARDIAC ARRHYTHMIA

(71) Applicant: Advanced Cooling Therapy, Inc., Chicago, IL (US)

(72) Inventors: Erik Kulstad, Chicago, IL (US); Patrick Shanley, Chicago, IL (US)

(73) Assignee: ADVANCED COOLING THERAPY, INC., Chicago, IL (US)

( * ) Notice: Subject to any disclaimer, the term of this patent is extended or adjusted under 35 U.S.C. 154(b) by 570 days.

(21) Appl. No.: 14/206,020

(22) Filed: Mar. 12, 2014

(65) Prior Publication Data

US 2014/0277305 A1    Sep. 18, 2014

Related U.S. Application Data

(60) Provisional application No. 61/779,496, filed on Mar. 13, 2013.

(51) Int. Cl.
| | |
|---|---|
| *A61F 7/12* | (2006.01) |
| *A61N 1/05* | (2006.01) |
| *A61N 1/39* | (2006.01) |
| *A61F 7/00* | (2006.01) |

(52) U.S. Cl.
CPC .............. *A61F 7/12* (2013.01); *A61N 1/0517* (2013.01); *A61N 1/39* (2013.01); *A61F 2007/0054* (2013.01)

(58) Field of Classification Search
CPC . A61F 7/12; A61F 2007/0054; A61N 1/0517; A61N 1/39
See application file for complete search history.

(56) References Cited

U.S. PATENT DOCUMENTS

| | | | |
|---|---|---|---|
| 4,351,330 A * | 9/1982 | Scarberry | A61M 16/04 128/207.15 |
| 4,735,206 A | 4/1988 | Hewson | |
| 5,052,390 A | 10/1991 | Hewson et al. | |
| 5,531,776 A * | 7/1996 | Ward | A61N 1/0517 128/898 |
| 5,716,386 A | 2/1998 | Ward et al. | |
| 6,607,517 B1 * | 8/2003 | Dae | A61F 7/12 604/31 |
| 8,231,664 B2 | 7/2012 | Kulstad et al. | |
| 2001/0005791 A1 * | 6/2001 | Ginsburg | A61F 7/12 607/106 |

(Continued)

OTHER PUBLICATIONS

Zerth, H., et al., "An inexpensive, easily constructed, reusable task trainer for simulating ultrasound-guided pericardiocentesis", J. Emerg. Med., Dec. 2012, 43(6), pp. 1066-1069.

*Primary Examiner* — Kaitlyn E Smith
*Assistant Examiner* — Yasamin Ekrami
(74) *Attorney, Agent, or Firm* — Neal, Gerber & Eisenberg LLP; Kevin A. O'Connor (57) ABSTRACT

Methods, devices, and systems for temperature management and ventricular defibrillation are disclosed. Methods, devices, and systems for positioning an electrode in the esophagus of a subject and managing the core body temperature of the subject are disclosed. The use of esophageal heat transfer devices to deliver an electrode for use in delivering an electrical shock to the myocardium is disclosed.

22 Claims, 3 Drawing Sheets

(56) References Cited

U.S. PATENT DOCUMENTS

| | | | |
|---|---|---|---|
| 2001/0047191 A1* | 11/2001 | Lasersohn | A61F 7/12 |
| | | | 607/3 |
| 2004/0230131 A1 | 11/2004 | Kassab et al. | |
| 2005/0015132 A1* | 1/2005 | Kronzon | A61B 8/12 |
| | | | 607/124 |
| 2007/0135875 A1* | 6/2007 | Demarais | A61F 7/123 |
| | | | 607/96 |
| 2008/0161890 A1* | 7/2008 | Lafontaine | A61B 18/1492 |
| | | | 607/105 |
| 2010/0057074 A1* | 3/2010 | Roman | A61B 18/1492 |
| | | | 606/33 |
| 2011/0012503 A1 | 1/2011 | Jackson | |
| 2011/0125234 A1 | 5/2011 | Kulstad et al. | |
| 2011/0130811 A1 | 6/2011 | Kulstad et al. | |
| 2012/0029321 A1* | 2/2012 | Makaretz | A61M 16/04 |
| | | | 600/301 |
| 2012/0143097 A1* | 6/2012 | Pike, Jr. | A61B 18/1492 |
| | | | 601/2 |
| 2012/0259329 A1* | 10/2012 | DeCarlo | A61B 18/1815 |
| | | | 606/42 |
| 2012/0265172 A1 | 10/2012 | Kulstad et al. | |
| 2013/0030425 A1* | 1/2013 | Stewart | A61B 18/02 |
| | | | 606/24 |
| 2013/0063336 A1 | 3/2013 | Sugimoto et al. | |
| 2014/0155965 A1 | 6/2014 | Kulstad et al. | |

* cited by examiner

DEVICES, SYSTEMS, AND METHODS FOR MANAGING PATIENT TEMPERATURE AND CORRECTING CARDIAC ARRHYTHMIA

RELATED APPLICATIONS

This application claims the priority of U.S. provisional application Ser. No. 61/779,496, filed on Mar. 13, 2013, which is incorporated by reference in its entirety.

FEDERALLY SPONSORED RESEARCH OR DEVELOPMENT

This invention was made with Government support under National Science Foundation (NSF) Award Number 1142664. The Government has certain rights in this invention.

FIELD OF THE INVENTION

The present technology relates to methods, devices, and systems for controlling core body temperature in a subject and providing at least one electrode within an esophagus of the subject. In one aspect, the present technology relates to a system that combines a device for controlling core body temperature of a subject with electrical devices for providing a defibrillating stimulus to the subject. In another aspect, the present technology relates to methods, devices, and systems for delivering an electrical shock to the heart of a subject while simultaneously managing the subject's core body temperature.

BACKGROUND OF THE INVENTION

Cardiac arrhythmias are disturbances in the normal rhythm of the heartbeat. Cardiac arrhythmias may be corrected by delivering an electric shock to the heart.

Ventricular fibrillation is an arrhythmia characterized by a rapid, irregular heart rhythm that may result in ineffective pumping of blood. Ventricular fibrillation is a frequent cause of cardiac arrest. Defibrillation is a reliable treatment for ventricular fibrillation. It is believed that the success of external defibrillation depends on the passage of an adequate current through the chest rather than on the administration of a preset energy.

Although the mechanism of defibrillation is not completely understood, it is believed that a defibrillating shock creates a voltage gradient though the myocardium and the extracellular space of the heart. This gradient drives current into cardiac cells facilitating defibrillation through alteration of the cellular transmembrane potential. If the voltage gradient created falls below the appropriate threshold, all of the fibrillating eddy currents may not terminate or new currents may be initiated, leading to redevelopment of fibrillation. Thus, it is desirable to deliver a large enough current in the appropriate waveform through a large enough amount of myocardial tissue to disrupt these eddy currents and restore unified depolarization. For example, it is desirable to provide a shock vector containing enough ventricular myocardium to disrupt the numerous eddy currents consuming the heart.

Hypothermia depresses cardiac ion channel conduction, which may contribute to sustained ventricular arrhythmias, including ventricular fibrillation. Although it has been observed that profound hypothermia does not hinder ventricular defibrillation in experimental animals where defibrillation is performed within seconds of ventricular fibrillation, the electrical disturbances provoked or exacerbated by hypothermia may adversely affect the ability to successfully defibrillate a patient.

Atrial fibrillation is an arrhythmia characterized by a rapid, irregular heart rhythm and occurs when the electrical impulses in the atria degenerate from their usual organized rhythm into a rapid chaotic pattern. Delivery of an electrical shock may be used as an emergency procedure when symptoms of very low blood pressure, chest pain, or heart failure caused by rapid, irregular atrial fibrillation are present.

Ventricular tachycardia is an arrhythmia characterized by a rapid heart rhythm that arises in the ventricle. During ventricular tachycardia, the output of the heart is decreased due to the rapid ventricular rate and the lack of properly timed or coordinated atrial contraction. In certain an emergency setting, for example, delivery of an electrical shock is also an effective treatment for ventricular tachycardia.

Cardioversion refers to a synchronized discharge of electrical current that is used to convert abnormal heart rhythms back to a normal rhythm. The electrical current is synchronized with the R or S wave of the QRS complex. It is believed that transient delivery of electrical current causes a depolarization of cardiac cells allowing the sinus node to resume normal pacemaker activity. For example, cardioversion may interrupt a self-perpetuating circuit underlying ventricular tachycardia and, thereby, restore a sinus rhythm.

BRIEF SUMMARY OF THE INVENTION

At least one aspect of the present technology provides an electrode lead wire adapted to be placed within the esophagus of a subject. In certain embodiments, the electrode lead wire is attached to or incorporated within an esophageal heat transfer device.

At least one aspect of the present technology provides an esophageal heat transfer device comprising at least one electrode lead wire. In certain embodiments, the electrode lead wire is attached to or incorporated within a heat transfer region of the heat transfer device.

At least one aspect of the present technology provides a system that combines a device for controlling core body temperature of a subject with electrical devices for providing a defibrillating stimulus to the subject. In certain embodiments, the system comprises an esophageal heat transfer device and at least one electrode lead wire. In certain embodiments, the electrode lead wire is capable of being attached to the esophageal heat transfer device. In certain embodiments, the electrode lead wire is attached to or incorporated within an esophageal heat transfer device.

At least one aspect of the present technology provides a system comprising an esophageal heat transfer device and at least one electrode lead wire. In certain embodiments, the electrode lead wire is capable of being attached to the esophageal heat transfer device.

At least one aspect of the present technology provides a method for controlling core body temperature in a subject and providing at least one electrode within an esophagus of the subject. The method comprises orally or nasally inserting an esophageal heat transfer device into a subject. The esophageal heat transfer device includes a heat transfer region that may be positioned within the subject's esophagus. In certain embodiments, an electrode lead wire is attached to or incorporated within a heat transfer region of the heat transfer device. In certain embodiments, the method includes inducing hypothermia or maintaining normothermia. In other embodiments, the method includes reducing core body temperature, maintaining core body temperature and/or raising core body temperature.

At least one aspect of the present technology provides a system to control core body temperature in a subject and providing at least one electrode within an esophagus of the subject. The system comprises an esophageal heat transfer device comprising at least one electrode lead wire. The heat transfer device is capable of being inserted nasally or orally and includes a heat transfer region that is capable of being positioned within the subject's esophagus. In certain embodiments, the electrode lead wire is attached to or incorporated within the heat transfer region of the heat transfer device.

At least one aspect of the present technology provides a method for delivering an electrical shock to the heart of a subject. The method comprises positioning a heat transfer region of a heat transfer device within the esophagus of the subject. The heat transfer device comprises at least one electrode lead wire. The electrode lead wire includes a proximal section that is connectable to a pulse generator. The method comprises connecting the lead wire to the pulse generator. The method further comprises generating a pulse or shock from the pulse generator. In certain embodiments, the electrode lead wire is attached to or incorporated within the heat transfer region of the heat transfer device. In certain embodiments, the method includes inducing hypothermia in the subject or reducing core body temperature in the subject. In certain embodiments, the subject is experiencing a cardiac arrhythmia.

At least one aspect of the present technology provides a system to deliver an electrical shock to the heart of a subject. The system comprises a heat transfer device comprising at least one electrode lead wire. The electrode lead wire includes a proximal section that is connectable to a pulse generator. The heat transfer device is capable of being nasally or orally inserted into a subject. The heat transfer device includes a heat transfer region capable of being positioned within the esophagus of the subject. In certain embodiments, the electrode lead wire is attached to or incorporated within the heat transfer region of the heat transfer device.

At least one aspect of the present technology provides a method for ventricular defibrillation. The method comprises positioning a heat transfer region of a heat transfer device within the esophagus of a subject. The heat transfer device comprises at least one electrode lead wire. The electrode lead wire includes a proximal section that is connectable to a pulse generator. The method comprises connecting the lead wire to the pulse generator. The method further comprises generating a pulse or shock from the pulse generator. In certain embodiments, the electrode lead wire is attached to or incorporated within the heat transfer region of the heat transfer device. In certain embodiments, the method includes inducing hypothermia in the subject or reducing core body temperature in the subject.

At least one aspect of the present technology provides a system to achieve ventricular defibrillation. The system comprises a heat transfer device comprising at least one electrode lead wire. The electrode lead wire includes a proximal section that is connectable to a pulse generator. The heat transfer device is capable of being nasally or orally inserted into a subject. The heat transfer device includes a heat transfer region capable of being positioned within the esophagus of the subject. In certain embodiments, the electrode lead wire is attached to or incorporated within the heat transfer region of the heat transfer device.

At least one aspect of the present technology provides a method for improving the likelihood of achieving ventricular defibrillation. The method comprises positioning an esophageal heat transfer device comprising at least one electrode lead wire into an esophagus of a subject. In certain embodiments, the electrode lead wire is attached to or incorporated within a heat transfer region of the heat transfer device. The method further includes inducing hypothermia in the subject or reducing core body temperature in the subject.

At least one aspect of the present technology provides a system to improve the likelihood of achieving ventricular defibrillation. The system comprises an esophageal heat transfer device comprising at least one electrode lead wire. In certain embodiments, the electrode lead wire is attached to or incorporated within a heat transfer region of the heat transfer device. The heat transfer region of the heat transfer device is capable of being positioned within an esophagus of the subject.

Other features, objects, and advantages of the present technology are apparent in the detailed description that follows. It should be understood, however, that the detailed description, while indicating embodiments of the present technology, are given by way of illustration only, not limitation. Various changes and modifications within the scope of the present technology will become apparent to those skilled in the art from the detailed description.

DETAILED DESCRIPTION OF THE INVENTION

At least one aspect of the present technology includes an electrode lead wire. In certain embodiments, the electrode lead wire comprises a distal section having at least one electrode and a proximal section capable of being connected to a pulse generator. In certain embodiments, the distal section of the electrode lead wire comprises multiple electrodes. The proximal section of the electrode lead wire may be connectable to the pulse generator directly or indirectly via, for example, another wire. In certain embodiments, the electrode lead wire comprises a conductive material suitable for transmission of an electrical signal from the pulse generator to the electrode. The electrode lead wire may also comprise an insulator material covering the conductive material.

At least one aspect of the present technology comprises placement of an electrode lead wire comprising a first electrode within a subject's esophagus. In certain embodiments, a second electrode may be placed on the subject's skin, thereby creating a path for current flow through the subject's myocardium. Placement of the second electrode on the subject's chest creates an anterior/posterior path for current flow through the subject's myocardium. The second electrode may be any type of external electrode, including, but not limited to, a paddle electrode, a wet-gel electrode, a solid-gel electrode, or an adhesive pad electrode. In certain other embodiments, a second electrode may be placed in the subject's esophagus.

At least one aspect of the present technology includes an esophageal heat transfer device. In certain embodiments, esophageal heat transfer devices such as those described in U.S. Pat. No. 8,231,664; US Patent Publication Nos. 2011/012503, 2011/0125234, 2011/0130811, 2012/0265172; and 2013/00063336; and U.S. patent application Ser. No. 13/768,752. The disclosures of each of the aforementioned patents, publications, and applications are hereby incorporated by reference in their entireties.

For example, an esophageal heat transfer device according to an embodiment of the present technology may comprise a heat transfer region that may be positioned within a subject's esophagus. The heat transfer region may be, for example, one or more sections of tubing. In certain embodiments, the esophageal heat transfer device may include a heat transfer medium supply tube and a heat transfer medium return tube. The heat transfer medium supply tube and heat transfer medium return tube may be arranged, for example, in parallel or concentrically. In one non-limiting example, the heat transfer medium return tube is positioned within a lumen defined by the heat transfer medium supply tube. In another non-limiting example, the heat transfer medium supply tube is positioned within a lumen defined by the heat transfer medium return tube. In still another non-limiting example, the heat transfer medium supply tube is positioned alongside the heat transfer medium return tube. The lumens of the heat transfer medium supply tube and heat transfer medium return tube may be in fluid communication with each other such that the heat transfer medium may flow along a fluid path defined by the lumens of the heat transfer medium supply tube and heat transfer medium return tube.

In certain embodiments, the flow rate of the heat transfer medium along the fluid path may be sufficient to prevent significant fluctuations in the temperature of the heat transfer medium as it flows along the fluid path. For example, the flow rate of the heat transfer medium may be from about 50 mL/min to about 1000 mL/min, preferably about 750 mL/min. As another example, the flow rate of the heat transfer medium may be sufficient to maintain the temperature of the heat transfer medium within about ±3° C., within about ±2° C., within about ±1° C., or within about ±0.5° C. between inlet and outlet temperature. In some embodiments, the flow rate of the heat transfer medium may be sufficient to maintain the temperature of the heat transfer medium within about ±0.1° C. between inlet and outlet temperature.

In certain embodiments, an esophageal heat transfer device may be configured for insertion into a nostril or mouth of a subject. When properly inserted, the heat transfer region of the heat transfer device may be ultimately positioned in the esophagus. Upon placement in the esophagus of a subject, the heat transfer region of the heat transfer device may be in direct contact with the subject's esophagus. In certain embodiments, the heat transfer region of the heat transfer device may contact substantially all of the epithelial surface of a subject's esophagus.

In certain embodiments, an esophageal heat transfer device may comprise one or more ports that allow for ingress and/or egress of the heat transfer medium. For example, the esophageal heat transfer device may include an input port for receiving a heat transfer medium from an external heat exchanger and an output port allowing the heat transfer medium to return to the heat exchanger. In certain embodiments, a supply line is connected to the input port and a return line is connected to the output port. In operation, heat transfer medium enters the input port, flows along a fluid path defined by one or more lumens, and exits the output port, thereby allowing for targeted temperature management. During this process, heat may be transferred from, for example, the heat transfer medium to the esophagus and adjacent organs, which ultimately results in warming the subject and/or maintaining core body temperature of the subject. Alternatively, heat may be transferred from, for example, the esophagus and adjacent organs to the heat transfer medium, which ultimately results in cooling the subject.

The heat transfer medium may be a gas (e.g., nitrous oxide, Freon, carbon dioxide, or nitrogen), liquid (e.g., water, saline, propylene glycol, ethylene glycol, or mixtures thereof), solid (e.g., ice, metal, metal alloy, or carbon fiber), slurry, and/or gel. In certain embodiments, a single lumen may function as both the inflow lumen and the outflow lumen. For example, heat transfer medium may be delivered to the heat transfer region and extracted from the heat transfer region via the single lumen by, for example, an external pump that alternatively pumps and withdraws heat transfer medium via the single lumen. In certain other embodiments, a solid heat transfer medium, which may comprise a heating element such as a wire or coil; a thermoelectric module such as a Peltier module; or a carbon fiber such as a graphitic carbon fiber, may be inserted into the single lumen.

In certain embodiments, an esophageal heat transfer device comprises one or more ports connected to one or more lumens, which provide a fluid path for the flow of heat transfer medium, and one or more gastric access tubes. For example, the esophageal heat transfer device may comprise an input port and an output port. The esophageal heat transfer device may further comprise one or more lumens that, physically or functionally, comprise a heat transfer medium supply lumen and a heat transfer medium return lumen. The heat transfer medium supply lumen and the heat transfer medium return lumen may be in fluid communication with each other, thereby defining a fluid path for the flow of the heat transfer medium. The esophageal heat transfer device may include one or more gastric access lumens that allows for gastric access when the device is positioned within a subject's esophagus.

In certain embodiments, heat transfer devices of the present technology include an inflatable heat transfer region. In other embodiments, heat transfer devices of the present technology include a heat transfer region that is not inflatable.

In certain embodiments, an esophageal heat transfer device may permit gastric access to the subject's health care provider. The heat transfer device may incorporate, for example, a gastric access lumen. The gastric access lumen may run parallel to a heat transfer medium supply tube and/or a heat transfer medium return tube. Alternatively, the gastric access lumen may be in a concentric arrangement with a heat transfer medium supply tube and/or a heat transfer medium return tube.

In certain embodiments, an esophageal heat transfer device includes a heat transfer region having a substantially helical configuration. For example, the heat transfer region may comprise a helical tube. A helical arrangement of the heat transfer region, or a portion thereof, allows for access to anatomical sites beyond the placement of the heat transfer device. The substantially helical configuration of the tube creates an interior space defined by the helix, which may comprise, for example, an access lumen. In some embodiments, the helical heat transfer region, or portion thereof, defines an access lumen. For example, when the helical heat transfer region, or portion thereof, is positioned within the esophagus, the access lumen allows for gastric access. A separate probe, such as a temperature probe, or separate tube, such as a nasogastric tube or an orogastric tube, can be inserted into the subject via the gastric access lumen. The nasogastric tube, orogastric tube, or probe may be provided with the heat transfer device or provided as an after-market component.

In certain embodiments, at least one of the gastric access lumens may allow for gastric suctioning. For example, the proximal end of a gastric tube defining a gastric lumen may be adapted to accommodate attachment to an external suctioning device. The distal portion of the gastric tube may include one or more ports that provide for communication between the space exterior to the gastric tube and the gastric access lumen. For example, one or more ports may act as a portal between the subject's stomach and the gastric access lumen allowing the gastric contents to be suctioned from the subject's stomach out through the gastric access lumen.

All or part of the heat transfer device may be manufactured by, for example, extrusion. Employing such a manufacturing modality eliminates the need to seal junctions or affix end caps and reduce the points at which leaks may occur. Alternatively, or additionally, a fast curing adhesive, such as RTV silicone sealant or temperature-curable sealant may be used to seal junctions and/or bond tubing together. The heat transfer device may be constructed using a biocompatible elastomer and/or plastic, and, optionally, adhesive. For example, biomedical grade extruded silicone rubber such as silicone rubber available from Dow Corning (e.g., Q7-4765, C6-165, and/or C6-550), and an adhesive such as Nusil Med2-4213 may be used to manufacture the heat transfer device.

At least one aspect of the present technology provides an electrode lead wire attached to or incorporated within a heat transfer region of an esophageal heat transfer device. The electrode lead wire comprises a distal section having at least one electrode and a proximal section capable of being connected to a pulse generator. The proximal section of the electrode lead wire may be connectable to the pulse generator directly or indirectly via, for example, another wire. In certain embodiments, the electrode lead wire comprises a conductive material suitable for transmission of an electrical signal from the pulse generator to the electrode. The electrode lead wire may also comprise an insulator material covering the conductive material. For example, one or more electrode lead wires may be affixed to the outer wall of a heat transfer medium supply tube or the outer wall of a heat transfer medium return tube. The electrode lead wire may be affixed to the outer wall with an adhesive. As another example, an electrode lead wire may be incorporated into the outer wall of a heat transfer medium supply tube or the outer wall of a heat transfer medium return tube. The electrode lead wire may be attached to or incorporated within the heat transfer region along any portion of the heat transfer region, including the distal and proximal portions of the heat transfer region. When the heat transfer region of the esophageal heat transfer device is positioned within the esophagus of a subject, the distal section of the electrode lead wire may be in close proximity to the subject's heart.

At least one aspect of the present technology provides a method for managing the core body temperature of a subject. The method comprises nasally or orally inserting an esophageal heat transfer device, which includes a heat transfer region, into a subject. The method further comprises positioning the heat transfer region within the subject's esophagus. The heat transfer device comprises one or more lumens, which define a fluid path for the flow of a heat transfer medium. The method further comprises initiating the flow of the heat transfer medium along the fluid path defined by the one or more lumens. In certain embodiments, the method includes inducing hypothermia or maintaining normothermia. In certain embodiments, the method may comprise reducing the core body temperature of the subject. Alternatively, the method may comprise maintaining core body temperature of the subject or raising the core body temperature of the subject. In certain embodiments, the heat transfer device also comprises at least one electrode lead wire. In certain embodiments, the electrode lead wire is capable of being attached to the esophageal heat transfer device. In certain embodiments, the electrode lead wire is attached to or incorporated within the esophageal heat transfer device.

At least one aspect of the present technology provides a system to manage the core body temperature of a subject. The system comprises a heat transfer device having a heat transfer region. The system may also comprise an external heat exchanger containing a heat transfer fluid; a pump for flowing the heat transfer fluid through a circuit within the heat transfer device; and/or a heat transfer element in contact with the external heat exchanger. The system may also comprise a sensor for detecting a parameter and generating a signal representative of the parameter, wherein the signal is transmitted to a microprocessor to control, for example, the flow of heat transfer fluid within the circuit. The sensor may be a pressure sensor positioned, for example, distal to the heat transfer region and configured to generate a signal representing the intra-abdominal, gastric or esophageal pressure of the subject. In certain embodiments, the system also comprises at least one electrode lead wire. In certain embodiments, the electrode lead wire is capable of being attached to the heat transfer device. In certain embodiments, the electrode lead wire is attached to or incorporated within the heat transfer device.

At least one aspect of the present technology provides a method for controlling core body temperature in a subject and providing at least one electrode within an esophagus of the subject. The method comprises orally or nasally inserting an esophageal heat transfer device having at least one electrode lead wire into a subject. In certain embodiments, the electrode lead wire is capable of being attached to a heat transfer region of the esophageal heat transfer device. In certain embodiments, the electrode lead wire is attached to or incorporated within the heat transfer region of the esophageal heat transfer device. The method further comprises positioning the heat transfer region within the subject's esophagus. The heat transfer device comprises one or more lumens, which define a fluid path for the flow of a heat transfer medium. The method further comprises initiating the flow of the heat transfer medium along the fluid path defined by the one or more lumens. In certain embodiments, the method includes inducing hypothermia or maintaining normothermia. In certain embodiments, the method may comprise reducing the core body temperature of the subject. Alternatively, the method may comprise maintaining core body temperature of the subject or raising the core body temperature of the subject.

At least one aspect of the present technology provides a system to control core body temperature in a subject and provide at least one electrode within an esophagus of the subject. The system comprises a heat transfer device having a heat transfer region and at least one electrode lead wire. In certain embodiments, the electrode lead wire is capable of being attached to the heat transfer region of the heat transfer device. In certain embodiments, the electrode lead wire is attached to or incorporated within the heat transfer region of the heat transfer device. The heat transfer device comprises one or more lumens, which define a fluid path for the flow of a heat transfer medium. The system may also comprise an external heat exchanger containing a heat transfer fluid; a pump for flowing the heat transfer fluid through a circuit within the heat transfer device; and/or a heat transfer element in contact with the external heat exchanger. The system may also comprise a sensor for detecting a parameter and generating a signal representative of the parameter, wherein the signal is transmitted to a microprocessor to control, for example, the flow of heat transfer fluid within the circuit. The sensor may be a pressure sensor positioned, for example, distal to the heat transfer region and configured to generate a signal representing the intra-abdominal, gastric or esophageal pressure of the subject. In certain embodiments, the system also comprises at least one electrode lead wire. In certain embodiments, the electrode lead wire is capable of being attached to the heat transfer device. In certain embodiments, the electrode lead wire is attached to or incorporated within the heat transfer device.

At least one aspect of the present technology provides a method for delivering an electrical shock to the heart of a subject while simultaneously managing the subject's core body temperature. The method comprises positioning a heat transfer region of a heat transfer device within the esophagus of the subject. The heat transfer device includes at least one electrode lead wire. The electrode lead wire includes a proximal section that is connectable to a pulse generator. The method comprises connecting the lead wire to the pulse generator. The method further comprises generating a pulse or shock from the pulse generator. In certain embodiments, the electrode lead wire is capable of being attached to the heat transfer region of the device. In certain embodiments, the electrode lead wire is attached to or incorporated within the heat transfer region of the device. In certain embodiments, the subject is experiencing a cardiac arrhythmia prior to delivery of the electrical shock. For example, the subject may be experiencing ventricular fibrillation prior to delivery of the electrical shock. In certain embodiments, the electrical shock may be a defibrillating shock. In certain embodiments, the electrical shock may be synchronized with the subject's cardiac cycle as in synchronized electrical cardioversion. In certain embodiments, multiple electrical shocks may be delivered over a brief period of time. In certain embodiments, the shock waveform may be, for example, monophasic or biphasic. In certain embodiments, the duration of the shock may be, for example, between about 5 and about 25 milliseconds, including about 5, about 10, about 15, about 20, and about 25 milliseconds. In one embodiment, the shock may be biphasic and, for example, comprise about 5 milliseconds of current flow in one direction followed by about 5 milliseconds of current flow in the reverse direction. Management of the subject's core body temperature may be achieved by the methods described herein and such management may occur before, during, and/or after delivery of the electrical shock. In certain embodiments, the method includes inducing hypothermia in the subject or reducing core body temperature in the subject before delivering the electrical shock.

At least one aspect of the present technology provides a system to deliver an electrical shock to the heart of a subject and simultaneously manage the subject's core body temperature. The system comprises a heat transfer device having a heat transfer region and at least one electrode lead wire. The electrode lead wire includes a proximal section that is connectable to a pulse generator. In certain embodiments, the electrode lead wire is capable of being attached to the heat transfer region of the device. In certain embodiments, the electrode lead wire is attached to or incorporated within the heat transfer region of the device. The heat transfer device comprises one or more lumens, which define a fluid path for the flow of a heat transfer medium. The system may also comprise an external heat exchanger containing a heat transfer fluid; a pump for flowing the heat transfer fluid through a circuit within the heat transfer device; and/or a heat transfer element in contact with the external heat exchanger. The system may also comprise a sensor. The sensor may be, for example, capable of monitoring heart rhythm or detect arrhythmias and/or other cardiac abnormalities. The sensor may also be capable of generating and transmitting a signal to a microprocessor, which may, for example, initiate or control the delivery of the electrical shock. The microprocessor may be coextensive with the pulse generator.

In certain embodiments, the devices, systems, and methods described herein encompass automatic defibrillation. For example, systems described herein may incorporate an automatic external defibrillator (AED). As one example, a device or system as described herein may incorporate a sensor, such as a detection electrode, to monitor the electrical activity of the heart. The detection electrode transmits a signal to the AED, which includes any available automatic defibrillation algorithm to determine if the electrical activity sensed by the detection electrode constitutes a shockable rhythm.

At least one aspect of the present technology provides a method for improving the likelihood of achieving ventricular defibrillation. The method comprises positioning a heat transfer region of a heat transfer device within the esophagus of the subject. The heat transfer device includes at least one electrode lead wire. The electrode lead wire includes a proximal section that is connectable to a pulse generator. The method comprises connecting the lead wire to the pulse generator. The method further comprises generating a pulse or shock from the pulse generator. In certain embodiments, the electrode lead wire is capable of being attached to the heat transfer region of the device. In certain embodiments, the electrode lead wire is attached to or incorporated within the heat transfer region of the device. In certain embodiments, the subject is experiencing a cardiac arrhythmia prior to delivery of the electrical shock. For example, the subject may be experiencing ventricular fibrillation prior to delivery of the electrical shock. In certain embodiments, the electrical shock may be a defibrillating shock. In certain embodiments, the electrical shock may be synchronized with the subject's cardiac cycle as in synchronized electrical cardioversion. In certain embodiments, multiple electrical shocks may be delivered over a brief period of time. In certain embodiments, the shock waveform may be, for example, monophasic or biphasic. In certain embodiments, the duration of the shock may be, for example, between about 5 and about 25 milliseconds, including about 5, about 10, about 15, about 20, and about 25 milliseconds. In one embodiment, the shock may be biphasic and, for example, comprise about 5 milliseconds of current flow in one direction followed by about 5 milliseconds of current flow in the reverse direction. Management of the subject's core body temperature may be achieved by the methods described herein and such management may occur before, during, and/or after delivery of the electrical shock. In certain embodiments, the method includes inducing hypothermia in the subject or reducing core body temperature in the subject before delivering the electrical shock.

At least one aspect of the present technology provides a system to improve the likelihood of achieving ventricular defibrillation. The system comprises a heat transfer device having a heat transfer region and at least one electrode lead wire. The electrode lead wire includes a proximal section that is connectable to a pulse generator. In certain embodiments, the electrode lead wire is capable of being attached to the heat transfer region of the device. In certain embodiments, the electrode lead wire is attached to or incorporated within the heat transfer region of the device. The heat transfer device comprises one or more lumens, which define a fluid path for the flow of a heat transfer medium. The system may also comprise an external heat exchanger containing a heat transfer fluid; a pump for flowing the heat transfer fluid through a circuit within the heat transfer device; and/or a heat transfer element in contact with the external heat exchanger. The system may also comprise a sensor. The sensor may be, for example, capable of monitoring heart rhythm or detect arrhythmias and/or other cardiac abnormalities. The sensor may also be capable of generating and transmitting a signal to a microprocessor, which may, for example, initiate or control the delivery of the electrical shock. The microprocessor may be coextensive with the pulse generator.

Devices, systems, and methods described herein improve the likelihood of achieving ventricular defibrillation as compared to currently available defibrillation modalities. For example and, without wishing to be bound by any particular theory, it is believed that the devices, systems, and methods described herein lower the defibrillation threshold and/or achieve increased amperage across the heart as compared to standard external defibrillation.

Devices, systems, and methods described herein reduce the energy needed to effectively defibrillate the heart. For example, the energy required to achieve defibrillation using devices, systems, and/or methods of the present technology can be from about 5 to about 30 J, including about 5, about 10, about 15, about 20, about 25, or about 30 J. As another example, the energy required to achieve defibrillation using devices, systems, and/or methods of the present technology can be less than 30 J.

The present technology now will be described with respect to the appended figures; however, the scope of the present technology is not intended to be limited thereby. It is to be understood that the scope of the present technology is not to be limited to the specific embodiments described herein. The technology may be practiced other than as particularly described and still be within the scope of the claims.

FIG. 1A-1D depicts a heat transfer device 100 according to an embodiment of the present technology. The heat transfer device 100 comprises a proximal section 102, a distal section 106, and a length of flexible tubing 104 extending therebetween. The length of flexible tubing 104 may comprise a heat transfer region. The distal section 106 of the heat transfer device 100 may be configured for insertion into a body orifice. For example, the distal section 106 of the heat transfer device 100 may be configured for insertion into the nostrils or mouth of a patient. When properly inserted, the heat transfer region of the heat transfer device 100 may be ultimately positioned in the esophagus, or other anatomical structure. Upon placement in, for example, the esophagus of a patient, the heat transfer region of the heat transfer device 100 can be in direct contact with the patient's esophagus. In certain embodiments, the heat transfer region of the heat transfer device 100 can contact substantially all of the epithelial surface of a patient's esophagus. The distal section 106 of the heat transfer device 100 may be configured to extend into a stomach of a patient.

All or part of the heat transfer device 100 can be manufactured by, for example, extrusion. Employing such a manufacturing modality would eliminate the need to seal junctions or affix end caps and reduce the points at which leaks may occur. Alternatively, or additionally, a fast curing adhesive, such as RTV silicone sealant or temperature-curable sealant can be used to seal junctions and/or bond tubing together. The heat transfer device 100 can be constructed using a biocompatible elastomer and/or plastic, and, optionally, adhesive. For example, biomedical grade extruded silicone rubber such as silicone rubber available from Dow Corning (e.g., Q7-4765, C6-165, and/or C6-550), and an adhesive such as Nusil Med2-4213 can be used to manufacture heat transfer device 100.

Figure 1A:
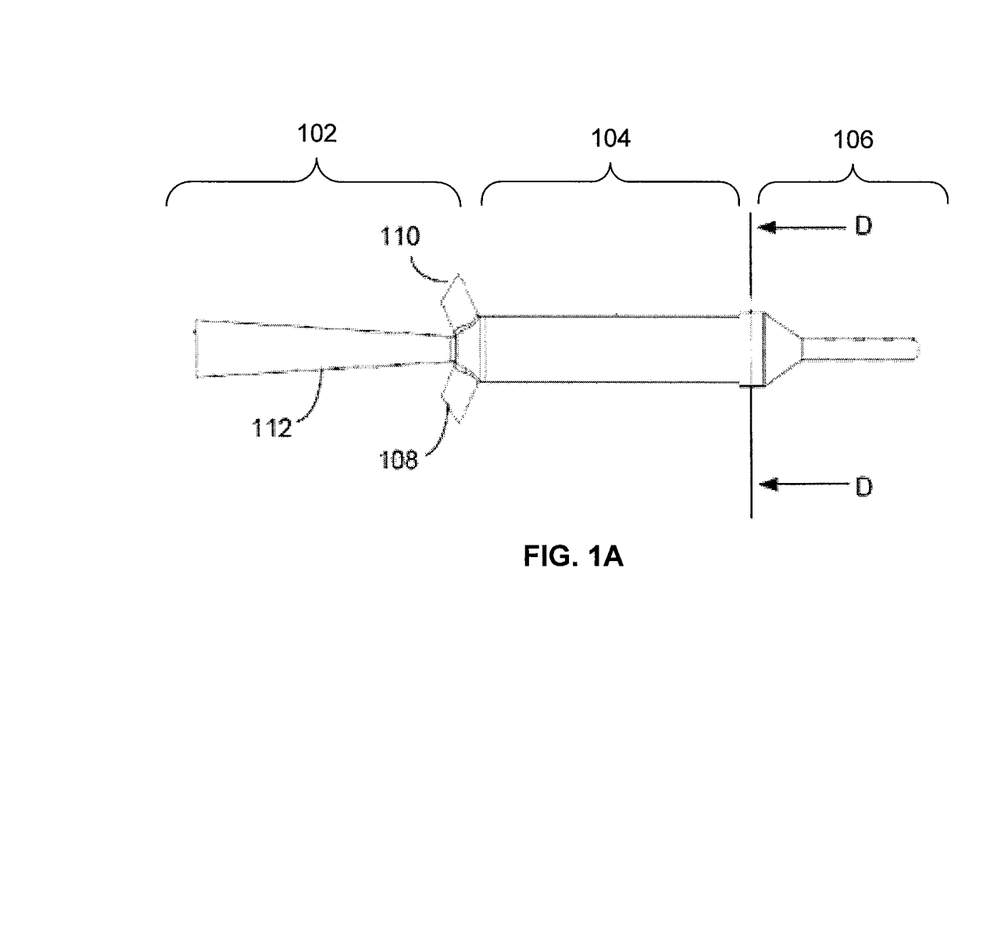
FIG. 1A-1D shows schematic views (FIGS. 1A and 1B) and cross-sectional views (FIGS. 1C and 1D) of a heat transfer device according to an exemplary embodiment of the present technology.

FIG. 1A shows a schematic view of the exterior of heat transfer device 100. The heat transfer device 100 includes an input port 108 and an output port 110. The heat transfer device 100 includes a gastric tube 112 that, for example, allows for gastric access. The proximal end of the gastric tube can be adapted to accommodate attachment to, for example, a suctioning device.

Figure 1B:
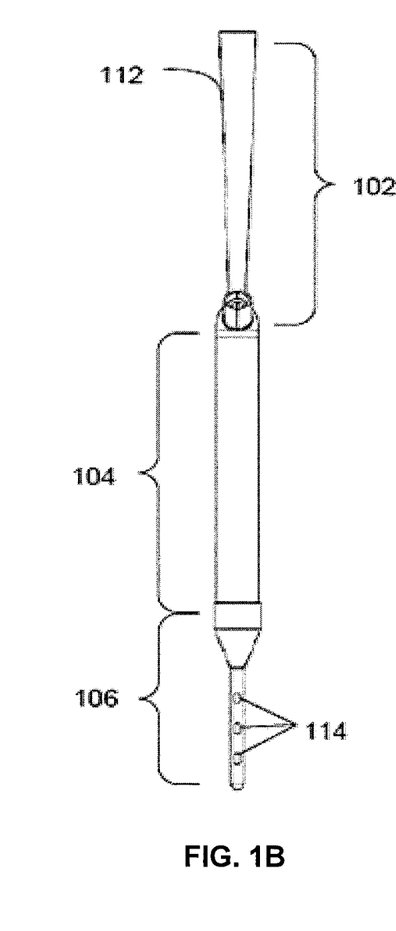
Figure 1C:
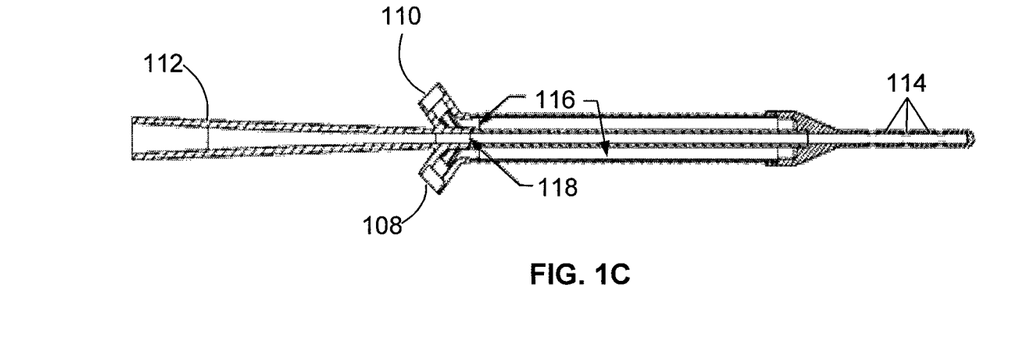

FIG. 1C is a cross-sectional view of the heat transfer device 100. The heat transfer device 100 comprises an internal cavity 116 and a gastric access tube 112. The gastric access tube 112 defines a gastric access lumen 118. As shown in FIGS. 1B and 1C, the distal section 106 of the heat transfer device 100 includes one or more ports 114 along the side of the gastric tube 112. The ports 114 may provide for communication between the space exterior to the device 100 and the gastric access lumen 118. For example, the ports 114 may act as a portal between the patient's stomach and the gastric access lumen 118 allowing the gastric contents to be suctioned from the patient's stomach out through the gastric access lumen 118. The presence of multiple ports 114 provides reduced likelihood of blockage of the gastric access lumen 118 from semi-solid stomach contents. Alternatively, multiple gastric access lumens may be employed. The addition of ports 114 may improve and enhance the removal of stomach contents, which, in turn, may improve contact between gastric mucosa and the heat transfer device 100. Such improved contact may enhance heat transfer between the heat transfer device 100 and the gastric mucosa. The configuration of the ports 114 shown in FIG. 1 is oval. However, the ports 114 can be, for example, circular, rectangular, or any other shape that permits flow of gastric contents from the stomach to the gastric access lumen 118.

Figure 1D:
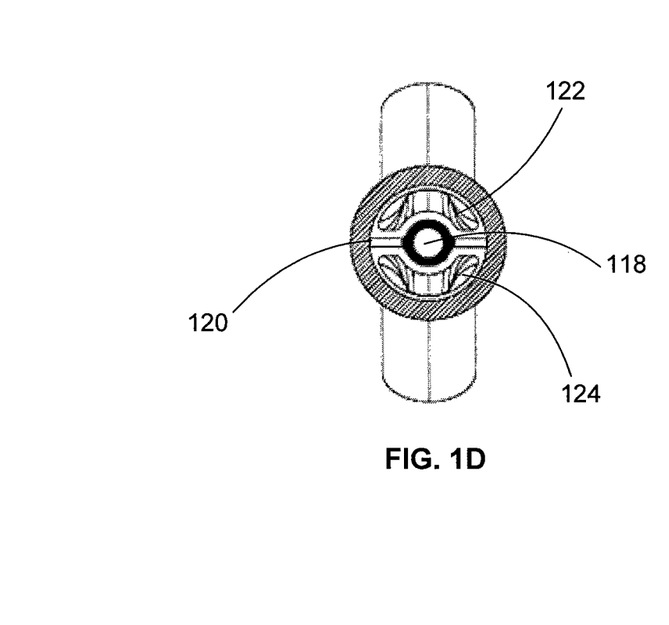

FIG. 1D is a cross-sectional view of the heat transfer device 100 along the line D-D shown in FIG. 1A. The internal cavity 116 can be divided by wall 120 into a multi-lumen cavity comprising, for example, a heat transfer medium supply lumen 122 and a heat transfer medium return lumen 124. The heat transfer medium supply tube lumen 122 and the heat transfer medium return tube lumen 124 may be in fluid communication with each other, thereby defining a fluid path for the flow of the heat transfer medium.

The gastric access lumen 118 is in a concentric arrangement with the interior cavity 116. As discussed above, the gastric access lumen 118 provides the health care professional with access to, for example, the patient's stomach while the heat transfer device 100 is positioned within the patient's esophagus.

Figure 2:
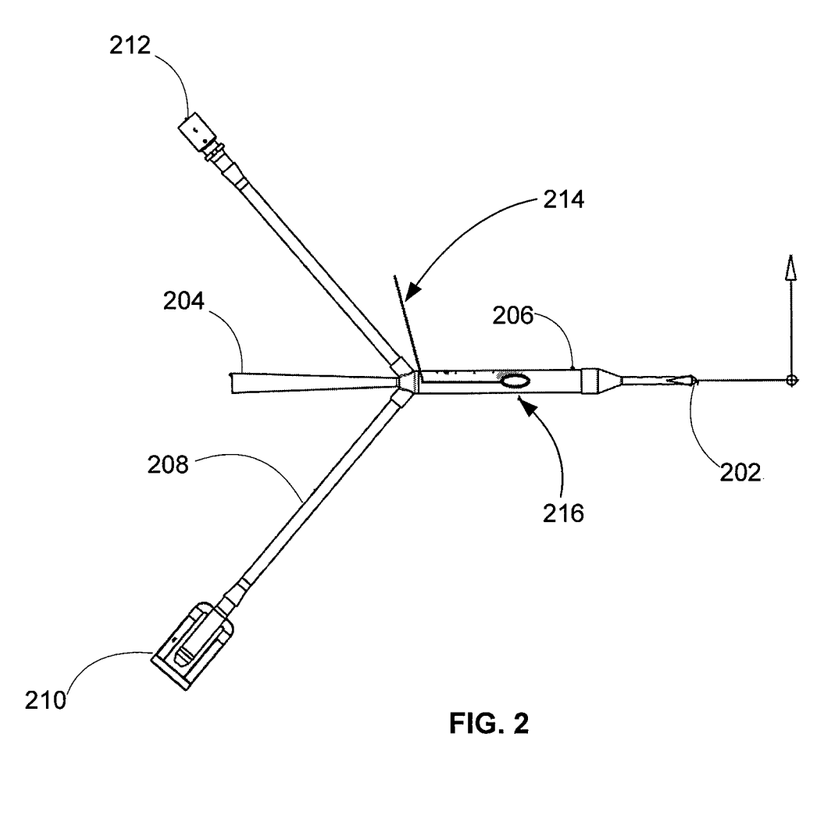
FIG. 2 shows a schematic diagram of a heat transfer system according to an exemplary embodiment of the present technology.

FIG. 2 depicts a heat transfer system 200 according to an embodiment of the present technology. The heat transfer system 200 comprises an esophageal heat transfer device having a distal end 202 and a proximal end cap 204.

The system 200 also comprises a tubular structure 206. Tubular structure 206 may be an extruded tube that defines a heat transfer medium supply lumen, a heat transfer medium return lumen, and/or a gastric access lumen. Tubular structure 206 may serve as a heat transfer region. In operation, part or all of tubular structure 206 may be positioned within a subject's esophagus. As such, the distal end 202 is positioned in an anatomical site, such as the stomach, that is distal to the position of tubular structure 206. The proximal end cap 204 may serve to extend the gastric access lumen, thereby providing the health care provider with more convenient access to anatomical sites that are distal to the heat transfer region.

The system 200 also comprises an external tube 208, which may be an external supply tube or an external return tube. The external tube 208 defines an external lumen providing a fluid path for flow of heat transfer medium from an external heat exchanger (not shown). The system also comprises connector 210 and connector 212 for connecting external tube 208 to the external heat exchanger. Connector 210 and connector 212 are, for example, press fit onto external tube 208. Connector 210 and connector 212 may be comprised of polypropylene.

The system 200 also comprises an electrode lead wire 214. The electrode lead wire 214 comprises a distal section having an electrode 216. The proximal section of the electrode lead wire 214 may be connectable to a pulse generator (not shown) directly or indirectly via, for example, another wire.

The electrode lead wire 214 may be affixed to the outer wall of tubular structure 206 with an adhesive. Alternatively, electrode lead wire 214 may be incorporated into the outer wall of tubular structure 206. Electrode lead wire 214 may be attached to or incorporated within the outer wall of tubular structure 206 along any portion of tubular structure 206, including the distal and proximal portions of tubular structure 206. In operation, when part or all of tubular structure 206 is positioned within the esophagus of a subject, electrode 216 may be in close proximity to the subject's heart.

As used herein, the words "a," "an," and "the" mean "one or more," unless otherwise specified. In addition, where aspects of the present technology are described with reference to lists of alternatives, the technology includes any individual member or subgroup of the list of alternatives and any combinations of one or more thereof.

The disclosures of all patents and publications, including published patent applications, are hereby incorporated by reference in their entireties to the same extent as if each patent and publication were specifically and individually incorporated by reference.

It is to be understood that the scope of the present technology is not to be limited to the specific embodiments described above. The present technology may be practiced other than as particularly described and still be within the scope of the accompanying claims.

Likewise, the following examples are presented in order to more fully illustrate the present technology. They should in no way be construed, however, as limiting the broad scope of the technology disclosed herein.

Example 1

An experiment was performed using a model thorax and myocardium as explained in detail in Zerth H, Harwood R, Tommaso L, Girzadas D V, Jr. An inexpensive, easily constructed, reusable task trainer for simulating ultrasound-guided pericardiocentesis. J Emerg Med. December 2012; 43(6):1066-1069). To measure amperage across the simulated myocardium during defibrillation, leads were placed adjacent to the model myocardium and connected to an ammeter. A Philips defibrillator was then connected to standard defibrillation/pacing pads, and the pads attached to the external surface of the model thorax. A series of measurements were then made with varying energy settings, ranging from 15 J to 170 J, and amperage across the myocardium was measured, demonstrating a mean of 510 microamps. Next, one of the defibrillator electrodes was placed circumferentially around a temperature management device according to an embodiment of the present technology, which was then placed into the simulated esophagus of the model thorax. The experiment was then repeated, with varying energy settings, ranging from 15 J to 170 J, and amperage across the myocardium was measured, demonstrating a mean of 620 microamps.

The foregoing description of the present technology provides illustration and description, but is not intended to be exhaustive or to limit the technology to the precise one disclosed. Modifications and variations are possible in light of the above teachings or may be acquired from practice of the technology.

What is claimed is:

1. A system to deliver an electrical shock to a heart of a subject and manage a core body temperature of the subject, the system comprising:
   an esophageal heat transfer device including an outer tube through which heat transfer medium is configured to flow, wherein the outer tube defines a non-inflatable heat transfer region that is configured to be positioned within an esophagus of the subject and transfer heat with the esophagus as the heat transfer medium flows through the outer tube to manage the core body temperature of the subject;
   an electrode configured to deliver the electrical shock to the heart of the subject when positioned within the esophagus proximate to the heart, wherein the electrode is coupled to the non-inflatable heat transfer region to enable the electrode to deliver the electrical shock to the heart from within the esophagus simultaneously as the non-inflatable heat transfer region transfers heat with the esophagus for managing the core body temperature of the subject; and
   an electrode lead wire including a distal end that is coupled to the electrode to enable the electrode to deliver the electrical shock.

2. The system of claim 1, wherein the electrode lead wire comprises a proximal section that is connectable to a pulse generator to further enable the electrode to deliver the electrical shock.

3. The system of claim 1, wherein the electrode lead wire is coupled to the outer tube of the non-inflatable heat transfer region.

4. The system of claim 3, wherein the electrode and the electrode lead wire are attached to a surface of the outer tube of the non-inflatable heat transfer region.

5. The system of claim 3, wherein the electrode and the electrode lead wire are incorporated within the outer tube of the non-inflatable heat transfer region.

6. The system of claim 3, wherein the heat transfer medium tube to which the electrode is coupled includes a heat transfer medium supply tube through which the heat transfer medium is provided to the non-inflatable heat transfer region and a heat transfer medium return tube through which the heat transfer medium is returned from the non-inflatable heat transfer region.

7. The system of claim 1, wherein the esophageal heat transfer device comprises an input port for receiving the heat transfer medium from an external reservoir and an output port for allowing the heat transfer medium to return to the external reservoir.

8. The system of claim 1, wherein, to manage the core body temperature of the subject, the esophageal heat transfer device is configured to decrease, increase, and maintain the core body temperature of the subject via the non-inflatable heat transfer region.

9. The system of claim 1, further including a second electrode to further deliver the electrical shock to the heart of the subject.

10. The system of claim 9, wherein the second electrode is configured to be coupled to be placed on a skin of the subject to create a path for current flow through a myocardium of the subject.

11. The system of claim 9, wherein the second electrode is coupled to the non-inflatable heat transfer region of the esophageal heat transfer device.

12. The system of claim 1, wherein the non-inflatable heat transfer region is configured to contact an epithelial surface of the esophagus to transfer heat with the esophagus of the subject.

13. A system for delivering an electrical shock to a heart of a subject and managing a body temperature of the subject, the system comprising:
   an esophageal heat transfer device including:
      a non-inflatable heat transfer region configured to be positioned within an esophagus of the subject to manage the core body temperature of the subject by transferring heat with the esophagus;
      at least one lumen defining a fluid path for flow of a heat transfer medium that enables the non-inflatable heat transfer region to transfer heat with the esophagus;
      at least one electrode configured to deliver the electrical shock to the heart of the subject when positioned within the esophagus proximate to the heart, wherein the at least one electrode is coupled to the non-inflatable heat transfer region to enable the at least one electrode to deliver the electrical shock to the heart from within the esophagus simultaneously as the non-inflatable heat transfer region transfers heat with the esophagus for managing the core body temperature; and at least one electrode lead wire including a distal end that is coupled to the at least one electrode to enable the at least one electrode to deliver the electrical shock; and an external reservoir capable of storing the heat transfer medium.

14. The system of claim 13, wherein the at least one electrode lead wire comprises a proximal end that is configured to connect to a pulse generator to further enable the at least one electrode to deliver the electrical shock.

15. The system of claim 13, further comprising a tubular wall that forms the non-inflatable heat transfer region.

16. The system of claim 15, wherein the at least one electrode and the at least one electrode lead wire are attached to a surface of the tubular wall of the non-inflatable heat transfer region.

17. The system of claim 15, wherein the at least one electrode and the at least one electrode lead wire are incorporated within the tubular wall of the non-inflatable heat transfer region.

18. The system of claim 13, wherein the esophageal heat transfer device comprises an input port for receiving the heat transfer medium from the external reservoir.

19. The system of claim 18, wherein the esophageal heat transfer device comprises an output port allowing the heat transfer medium to return to the external reservoir.

20. The system of claim 13, wherein the at least one lumen is defined by a heat transfer medium supply tube and a heat transfer medium return tube, wherein the heat transfer medium supply tube and the heat transfer medium return tube are arranged concentrically.

21. The system of claim 13, wherein the non-inflatable heat transfer region is configured to contact an epithelial surface of the esophagus to transfer heat with the esophagus of the subject.

22. A system for delivering an electrical shock to a heart of a subject and managing a body temperature of the subject, the system comprising:
   an esophageal heat transfer device including:
      a non-inflatable heat transfer region configured to be positioned within an esophagus of the subject to manage the core body temperature of the subject by transferring heat with the esophagus;
      at least one lumen defining a fluid path for flow of a heat transfer medium that enables the non-inflatable heat transfer region to transfer heat with the esophagus;
      at least one electrode configured to deliver the electrical shock to the heart of the subject when positioned within the esophagus proximate to the heart, wherein the at least one electrode is coupled to the non-inflatable heat transfer region to enable the at least one electrode to deliver the electrical shock to the heart from within the esophagus when the non-inflatable heat transfer region is positioned within the esophagus to transfer heat with the esophagus for managing the core body temperature, wherein the at least one electrode is coupled to the non-inflatable heat transfer region to enable the at least one electrode to be proximate to the heart of the subject for delivering the electrical shock to the heart simultaneously as the non-inflatable heat transfer region transfers heat with the esophagus of the subject; and
      at least one electrode lead wire including a distal end that is coupled to the at least one electrode to enable the at least one electrode to deliver the electrical shock; and
   an external reservoir capable of storing the heat transfer medium.

\* \* \* \* \*